United States Patent
Langlade Demoyen et al.

(10) Patent No.: US 10,493,154 B2
(45) Date of Patent: Dec. 3, 2019

(54) GENE ELECTROTRANSFER INTO SKIN CELLS

(71) Applicants: INVECTYS, Paris (FR); Centre National De La Recherche Scientifique, Paris (FR)

(72) Inventors: Pierre Langlade Demoyen, Neuilly-sur-Seine (FR); Thierry Huet, Nogent sur Marne (FR); Christelle Liard, Chatillon (FR); Jessie Thalmensi, Villeneuve la Garenne (FR); Luis M. Mir, Verrieres le Buisson (FR); Christophe Calvet, Paris (FR)

(73) Assignees: INVECTYS, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 316 days.

(21) Appl. No.: 15/032,754

(22) PCT Filed: Oct. 28, 2014

(86) PCT No.: PCT/EP2014/073159
§ 371 (c)(1),
(2) Date: Apr. 28, 2016

(87) PCT Pub. No.: WO2015/063112
PCT Pub. Date: May 7, 2015

(65) Prior Publication Data
US 2016/0279244 A1    Sep. 29, 2016

(30) Foreign Application Priority Data
Oct. 28, 2013   (EP) ..................................... 13190550

(51) Int. Cl.
| | | |
|---|---|---|
| A61K 41/00 | (2006.01) | |
| C12N 15/87 | (2006.01) | |
| A61K 39/00 | (2006.01) | |
| A61K 48/00 | (2006.01) | |
| A61N 1/04 | (2006.01) | |
| A61N 1/32 | (2006.01) | |

(52) U.S. Cl.
CPC .......... *A61K 41/0047* (2013.01); *A61K 39/00* (2013.01); *A61K 39/0011* (2013.01); *A61K 48/0075* (2013.01); *A61N 1/0428* (2013.01); *C12N 15/87* (2013.01); *A61K 2039/53* (2013.01); *A61K 2039/54* (2013.01); *A61N 1/327* (2013.01)

(58) Field of Classification Search
CPC .......... A61K 41/0047; A61K 39/00; A61K 39/0011; A61K 48/0075; A61K 2039/53; A61K 2039/54; A61N 1/0428; A61N 1/327; C12N 15/87
See application file for complete search history.

(56) References Cited

U.S. PATENT DOCUMENTS

| | | |
|---|---|---|
| 5,539,084 A | 7/1996 | Geysen |
| 5,840,839 A | 11/1998 | Wang et al. |
| 8,003,773 B2 | 8/2011 | Langlade-Demoyen et al. |
| 8,222,392 B2 | 7/2012 | Cech et al. |
| 2003/0143228 A1 | 7/2003 | Chen et al. |
| 2004/0106128 A1* | 6/2004 | Majumdar ........... C12N 9/1276 435/6.18 |
| 2008/0090778 A1 | 4/2008 | Scarselli et al. |
| 2009/0175892 A1 | 7/2009 | Langlade-Demoyen et al. |
| 2009/0269739 A1 | 10/2009 | Cech et al. |
| 2011/0318380 A1 | 12/2011 | Brix et al. |
| 2016/0051650 A1 | 2/2016 | Langlade-Demoyen et al. |
| 2016/0347798 A1 | 12/2016 | Poma et al. |

FOREIGN PATENT DOCUMENTS

| | | | |
|---|---|---|---|
| JP | 2009507786 A | 2/2009 | |
| WO | 1998014593 A2 | 4/1998 | |
| WO | 2003038047 A2 | 5/2003 | |
| WO | 2008043760 A1 | 4/2008 | |
| WO | WO-2011073796 A2 * | 6/2011 | .............. A61M 5/32 |

OTHER PUBLICATIONS

Kay, Nature Reviews Genetics, advance online publication, pp. 1-13, published online Apr. 6, 2011.*
Misra, JAPI 61: 127-133, 2013.*
English Translation of Japanese Office Action Issed in JP2016-504709, dated Oct. 10, 2017, 5 pages.
English Translation of Japanese Office Action Issed in JP2016-504710, dated Oct. 10, 2017, 6 pages.
Cadile, C. D. et al., "Telomerase activity as a marker for malignancy in feline tissues", American Journal of Veterinary Research (2001), vol. 62, No. 10, pp. 1578-1581.
Huang, J. J. et al., "Ectopic Expression of a COOH-terminal Fragment of the Human Telomerase Reverse Transcriptase Leads to Telomere Dysfunction and Reduction of Growth and Tumorigenicity in HeLa Cells", Cancer Research (2002), vol. 62, pp. 3226-3232.
Huo, L. et al., "Cancer Immunotherapy Targeting the Telomerase Reverse Transcriptase" Cellular and Molecular Immunology (2006), vol. 3, No. 1, pp. 1-9.
Impellizeri, J. A. et al., "Electro-gene-transfer as a new tool for cancer immunotherapy in animals", Veterinary and Comparative Oncology, Short Communication, (Oct. 24, 2012), vol. 12, issue 4, pp. 1-9; DOI: 10.1111/vco.12006.
Ng, SSM et al., "A novel glioblastoma cancer gene therapy using AAV-mediated long-term expression of human TERT C-terminal polypeptide", Cancer Gene Therapy (2007), vol. 14, pp. 561-572.

(Continued)

Primary Examiner — Thaian N Ton
(74) Attorney, Agent, or Firm — Troutman Sanders LLP

(57) ABSTRACT

The present invention relates to methods for transferring a nucleic acid in vivo into skin cells wherein the nucleic acid is injected by intradermal (ID) injection and is electrically transferred into skin cells with a single pulse of a High Voltage, followed, after a defined lag time, by a single pulse of Low Voltage.

15 Claims, 3 Drawing Sheets

(56) References Cited

OTHER PUBLICATIONS

Figure 1:
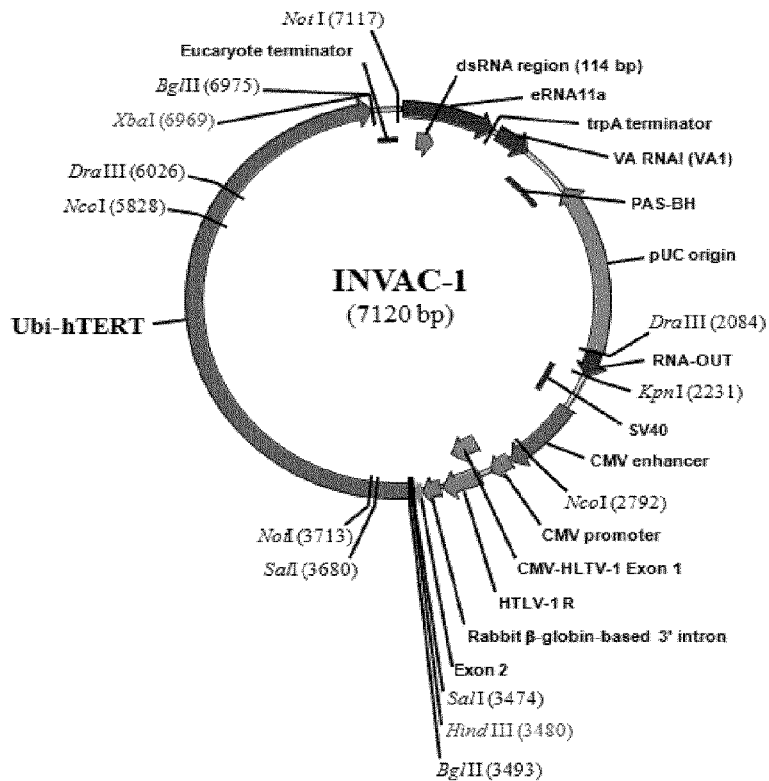

André, F. M. et al., "Efficiency of High- and Low-Voltage Pulse Combinations for Gene Electrotransfer in Muscle, Liver, Tumor, and Skin", Human Gene Therapy (2008), vol. 19:11, p. 1261-1271.
Banga, Ajay K. et al., "Iontophoresis and electroporation: comparisons and contrasts", International Journal of Pharmaceutics (1999), vol. 179:1, p. 1-19.
Gothelf, Anita et al., "Efficacy of transgene expression in porcine skin as a function of electrode choice", Bioelectrochemistry (2011), vol. 82:2, p. 95-102.
Payselj, N. et al., "DNA electrotransfer into the skin using a combination of one high- and low-voltage pulse", Journal of Controlled Release (2005), vol. 106:3, p. 407-415.
Satkauskas, Saulius et al., "Electrophoretic Component of Electric Pulses Determines the Efficacy of In Vivo DNA Electrotransfer", Human Gene Therapy (2005), vol. 16:10, p. 1194-1201.
PCT/EP2014/073159 International Search Report and Written Opinion dated Jan. 5, 2015, 8 pages.
Adotevi, Olivier et al. "Immunogenic HLA-B*0702-Restricted Epitopes Derived from Human Telomerase Reverse Transcriptase that Elicit Antitumor Cytotoxic T-Cell Responses" Clin Cancer Res (2006), vol. 12, No. 10, pp. 3158-3167.
Adotevi, Olivier et al. "Targeting human telomerase reverse transcriptase with recombinant lentivector is highly effective to stimulate antitumor CD8 T-cell immunity in vivo" Blood (2010) vol. 115, No. 15, pp. 3025-3032.
Andersson, H.A. et al., "Maximizing Antigen Targeting to the Proteasome for Gene-Based Vaccines" Molecular Therapy (2004) vol. 10, No. 3, pp. 432-446.
Armbruster, B.N. et al., "N-Terminal Domains of the Human Telomerase Catalytic Subunit Required for Enzyme Activity in Vivo" Molecular and Cellular Biology (2001) vol. 21, No. 22, pp. 7775-7786.
Artandi, Steven E. et al., "Telomeres and telomerase in cancer". Carcinogenesis (2010) vol. 31, No. 1, pp. 9-18.
Bevan, Michael J., "Helping the CD8+ T-Cell Response" Nature Reviews Immunology (2004) vol. 4, pp. 595-602.
Bolonaki, Irini et al., "Vaccination of Patients with Advanced Non-Small-Cell Lung Cancer With an Optimized Cryptic Human Telomerase Reverse Transcriptase Peptide" Journal of Clinical Oncology: Official Journal of the American Society of Clinical Oncology (2007) vol. 25, No. 19, pp. 2727-2734.
Delogu, G. et al., "DNA Vaccine Combinations Expressing Either Tissue Plasminogen Activator Signal Sequence Fusion Proteins or Ubiquitin-Conjugated Antigens Induce Sustained Protective Immunity in a Mouse Model of Pulmonary Tuberculosis" Infection and Immunity (2002) vol. 70, No. 1, pp. 292-302.
Drosopoulos, W.C. et al., "The active site residue Valine 867 in human telomerase reverse transcriptase influences nucleotide incorporation and fidelity" Nucleic Acids Research (2007) vol. 35, No. 4, pp. 1155-1168.
European Communication Pursuant to Article 94(3) EPC issued in EP14716530.2 and dated Jan. 17, 2017, 5 pages.
European Communication Pursuant to Article 94(3) EPC issued in EP14790592.1 and dated May 30, 2017, 4 pages.
Yang, Yinhua et al., "Nucleolar Localization of hTERT Protein is Associated with Telomerase Function" Experimental Research (2002) vol. 277, No. 2, pp. 201-209.
European Search Report and Opinion dated Sep. 24, 2012, which issued during prosecution of European Application No. 12305319.1, 7 pages.
Godet, Vann et al. "Analysis of Spontaneous Tumor-Specific CD4 T-cell immunity in Lung Cancer Using Promiscuous HLA-DR Telomerase-Derived Epitopes: Potential Synergistic Effect with Chemotherapy Response" Clinical Cancer Research; An Official Journal of the American Association for Cancer Research (2012) vol. 18, No. 10, pp. 2943-2953.
Hanahan, Douglas et al., "Hallmarks of Cancer: The Next Generation" Cell (2014) vol. 144, pp. 646-674.
International Preliminary Report on Patentability dated Sep. 29, 2015 during prosecution of International Patent Application No. PCT/EP2014/056381, 8 pages.
International Preliminary Report on Patentability Issued in International Application No. PCT/EP2013/054592 dated Sep. 16, 2014, 5 pages.
International Preliminary Report on Patentability Issued in International Application No. PCT/EP2014/073164 dated May 3, 2016, 6 pages.
International Search Report and Written Opinion of the International Searching Authority dated Apr. 12, 2013, which issued during prosecution of International Application No. PCT/EP2013/054592, 13 pages.
International Search Report and Written Opinion of the International Searching Authority dated Feb. 4, 2015, which issued during prosecution of international Application No. PCT/EP2014/073164, 10 pages.
International Search Report and Written Opinion of the International Searching Authority dated Jul. 2, 2014, which issued during prosecution of International Application No. PCT/EP2014/056381.
International Search Report and Written Opinion of the International Searching Authority issued in PCT/EP2014/056380, dated Jul. 23, 2014, 14 pages.
Kiecker, Felix et al., "Analysis of Antigen-Specific T-Cell Responses With Synthetic Peptides-What Kind of Peptide for Which Purpose?" Human Immunology (2004) vol. 65, pp. 523-536.
Klebanoff, Christopher A. et al., "Therapeutic cancer vaccines: are we there yet?" Immunology Reviews (2011) vol. 239, pp. 27-44.
Kyte, Jon Amund et al., "Telomerase Peptide Vaccination Combined with Temozolomide: A Clinical Trial in Stage IV Melanoma Patients", Clinical Cancer Research (2011) vol. 7, No. 13, pp. 4568-4580.
Martinez, Paula et al., "Telomeric and extra-telomeric roles for telomerase and the telomere-binding proteins" Reviews Cancer (2011) vol. 11, pp. 161-176.
Muller, S., "Ubiquitin" Manual of Biological Markers of Disease (1994) B2, 3, pp. 1-11.
NCBI Reference Sequence NM_198253.2, *Homo sapiens* telomerase reverse transcriptase (TERT), transcript variant 1, Mrna, 8 pages, Oct. 27, 2012.
NCBI reference sequence XP_019669508.1, Predicted: Low Quality Protein: telomerase reverse transcriptase, partial [Feliscatus], dated Dec. 29, 2016, pp. 1-2, 2 pages.
NCBI Sequence AAC51724.1, Telomerase catalytic subunit [*Homo sapiens*], dated Aug. 28, 1997, 2 pages.
Osen. Wolfram et al., Screening of Human Tumor Antigens for CD4+ T Cell Epitopes by Combination of HLA-Transgenic Mice, Recombinant Adenovirus and Antigen Peptide Libraries PLoS One (2010) vol. 5, Issue 11, p. e14137.
Peruzzi, D., et al., "Telomerase and HER-2/neu as targets of genetic cancer vaccines in dogs" Vaccine (2010) vol. No. 5, pp. 1201-1208.
Peruzzi, Daniela, et al., ""A Vaccine Targeting Telomerase Enhances Survival of Dogs Affected by B-cell Lymphoma"" Therapy (2010) vol. 18, No. 8, pp. 1559-1567.
Reay, Philip et al., ""Use of Global Amino Replacements to Define the Requirements for MHC Binding and T Cellof of Moth Cytochrome. c (93-103)"" Journal of Immunology (1994) vol. 152, pp. 3946-3957.
Ruden, Maria et al., ""Novel anticancer therapeutics targeting telomerase"" Cancer Treatment Reviews (2013) vol. 39, 5, pp. 444-456.
Scardino, Antonio et al, HER-2/neu and hTERT Cryptic Epitopes as Novel Targets for Broad Spectrum Tumor the Journal of Immunology (2002) vol. 168, pp. 5900-5906.
Schlapbach, Christoph et al., "Telomerase-specific GV1001 peptide vaccination fails to induce objective tumor response in patients with cutaneous 1 cell lymphoma" Journal of Dermatological Science (2011) vol. 62. No. 2, pp. 75-83.
Schroers, Roland et al. "Identification of HLA DR7-restricted Epitopes from Human Telomerase Reverse Transcriptase Recognized by CD4+ T-Helper Cells" Cancer Research, American Association for Cancer Research (2002) vol. 62, No. 9, pp. 2600-2605.
Schroers, Roland et al., "Human Telomerase Reverse Transcriptase-Specific T-Helper Responses Induced by Promiscuous Major

(56) References Cited

OTHER PUBLICATIONS

Histocompatibility Complex Class it-Restricted Epitopes" Clinical Cancer Research: An Official Journal of the American Association for Cancer Research (2003) vol. 9, No, 13, pp. 4743-4755.
"Velders, M. P. et al., ""Defined Flanking Spacers and Enhanced Proteolysis Is Essential for Eradication ofTumors by an Epitope String DNA Vaccine"" Journal Immunology (2001) vol. 166, pp. 5366-5373."
Wang, Qingmin et al., "Improved Cellular Immune Response Elicited by a Ubiquitin-Fused DNA Vaccine Against *Mycobacterium tuberculosis*", DNA and Cell Biology (2012) vol. 31, No. 4, pp. 489-495.
Yamano, T. et al., "Immunity Against Breast Cancer by TERT DNA Vaccine Primed with Chemokine CCL21" Cancer Gene Therapy (2007) vol. 14, pp. 451-459.
Song, J-M., "DNA Vaccination in the Skin Using Microneedles Improves Protection Against Influenza" The American Society of Gene & Cell Therapy (2012) vol. 20, No. 7, pp. 1472-1480.

\* cited by examiner

GENE ELECTROTRANSFER INTO SKIN CELLS

CROSS-REFERENCE TO RELATED APPLICATIONS

This application is the U.S. National Phase application under 35 U.S.C. § 371 of International Patent Application No. PCT/EP2014/073159, filed on Oct. 28, 2014, which claims priority to European Patent Application No. EP 13190550.7, filed on Oct. 28, 2013, both of which applications are incorporated herein by reference in their entireties.

BACKGROUND OF THE INVENTION

Cell electropermeabilization, that is to say cell permeabilization via the local delivery of electric pulses (EP), is increasingly used for the management and prevention of a wide range of human and animal pathologies, including cancer.

Cell membrane delimits two compartments, the cytoplasm and the extracellular medium, that present different ions concentrations thus creating a difference in the transmembrane potential. When an electric field is applied to the cells, it results on an induced transmembrane potential which superimposes the resting one (Mir et al., 2005). Above a threshold, a transient permeabilization occurs leading to an exchange of molecules between the cytoplasm and the external medium. This phenomenon consequent to the application of EP to the cells and leading to the loss of membrane permeability is called electropermeabilization. This technique has been used for three decades to enhance non permeant molecules uptake by cells.

Although the exact mechanism of electropermeabilization is still subject to debate, this technique paved the way for many biomedical applications, in particular for cancer treatments (Breton & Mir, 2011). One of them, called antitumor electrochemotherapy, consists in coupling EP directly applied to the tumor site with the administration of bleomycin or cisplatin, which do not spontaneously diffuse (or poorly) through the plasma membrane (Mir et al., 1991; Mir, 2006). Once entering the electropermeabilized cells, these two drugs generate DNA damages and trigger cell death. Not only drugs but also nucleic acids, which are non permeant molecules (Satkauskas et al., 2002; Andre & Mir, 2010), can be electrotransferred into cells using electropermeabilization. DNA has been successfully transferred into various tissues of living animals including skin, muscle, liver, tumor, cornea, lung, kidney, brain, bladder and testis (reviewed in Andre et al., 2008; Gothelf & Ghel, 2010). One promising use of the gene electrotransfer method concerns the field of DNA vaccination. Indeed, DNA vaccination has raised a great excitement since the early 90's. Wolff and collaborators first managed to transfer DNA into animal muscles. Once transfected, DNA molecules allowed the target cells to produce the encoded protein (Wolff et al., 1990). Tang et al. demonstrated that a protein encoded by a DNA transferred to skin cells by a biolistic method could trigger an immune response (Tang et al., 1992) and Barry et al. showed that gene vaccination with a plasmid encoding a pathogen protein protected the animals against a challenge with the relevant pathogen (Barry et al., 1995). This technology has been used for a wide range of applications from laboratory tools to licensed veterinary vaccines (Anderson et al., 1996) and is under development for the management of various acquired pathologies such as cancer, malaria, hepatitis B and C or for the prevention of some viral infections such as influenza or human immunodeficiency virus (clinicaltrials.gov) (Bergman et al., 2003).

Eventually, DNA vaccines possess manufacturing, accessibility and economic advantages compared to other vaccine technologies (Liu, 2011). Despite the fact that DNA vaccines offer a precise and flexible strategy for delivering antigens to immune cells and to mount a specific immune response, there were issues at the beginning for translating this technique from small rodents to larger animals and in fine to patients (Rochard et al., 2011). As a matter of fact, DNA vaccines were found to be weakly immunogenic partially due to the low cellular uptake of DNA molecules at the site of vaccination. This problem has been overcome by using gene electrotransfer which dramatically improves the performance of DNA vaccines (Li et al., 2012; Gothelf & Gehl, 2012).

However, in order to use electrotransfer as expected for vaccination strategies, the procedure has to be performed with a very specific procedure. Electrotransfer is a multistep process that relies on two different types of EP (Andre & Mir, 2010; Satkauskas et al., 2005; Favard et al., 2007). First, DNA has to be brought close to the target cells environment by injection at the expected site of vaccination (skin, muscle), then one or several short (about one hundred of microseconds) and intense (about one thousand volts per centimeter) pulses, called high voltage (HV) pulses, permeabilize reversibly the cell membrane. A defined lag time later, one or several long (about several hundred of milliseconds) and less intense (about one hundred volts per centimeter) pulses, called low voltage (LV) pulses are applied. LV pulses are meant to drive electrophoretically the DNA throughout the extracellular matrix all the way to the contact with the electropermeabilized membrane. At this point, no consensus exists regarding how DNA molecules cross the plasma membrane and get to the nucleus to be taken in charge by cell translational machinery (Escoffre et al., 2009).

Interestingly, no serious side effect was ever detected either in animals or in humans after DNA administration followed by electrotransfer (Fioretti et al., 2013). A study reported that after administration, a DNA vaccine was mostly located around the site of the injection, its local detection levels decreased rapidly over time, no gonadal tissue internalized it (very low risk of germ-line transmission) and the integration probability was very low since no viral protein was used (Dolter et al., 2011). Moreover, when DNA molecules are used for vaccination purposes along with the gene electrotransfer method, there is no pre- or post-treatment immunity issues contrary to viral vectors such as adenoviral vectors, thus allowing multiple administrations (homologous prime-boost DNA/DNA or heterologous prime-boost DNA/vector or DNA/protein) (Villemejane & Mir, 2009). Consequently, DNA vaccination combined with electrotransfer has gained interest in the last few years.

For what concerns the cancer pathology, DNA vaccines are meant to trigger an immune response against tumor-specific or tumor-associated antigens (Stevenson & Palucka, 2010). Indeed, cancer cells fool the immune system that cannot always efficiently initiate an immune response due to multiple complex mechanisms such as self-tolerance (Bei & Scardino, 2010), diverse immunosuppression mechanisms involving either regulatory T-cells or myeloid-derived suppressor dendritic cells (moDCs) (Lindau et al., 2013), molecules expressed at the surface of immune cells such as CTLA-4 (Kolar et al, 2009; Shevach, 2009) and PD-1/PD-1L interaction (Keir et al., 2008).

The ultimate goal of an efficient DNA vaccine delivered via the electrotransfer technology must be to generate the right kind of immune responses against the antigen encoded by the plasmid of interest. Although well described for intramuscular administration route (patent application WO 2007/026236) (Mir et al., 2005; Andre & Mir, 2010), very few is known about electrotransfer parameters in the skin, for vaccination purposes. The immune response should be intense enough and long lasting enough to generate positive therapeutic effects in patients with a specific pathology. Of note, the intensity of the immune response depends, at least partially, on the level of antigen expression (Lee et al., 1997; Kirman & Seder, 2003), which is itself closely correlated to the efficacy of gene transfer. Regarding gene electrotransfer efficiency in skin, it depends on several parameters including the intensity of EP and the type of electrodes used to deliver them (Gothelf & Gehl, 2010).

BRIEF DESCRIPTION OF THE INVENTION

The inventors have found that electrotransfer efficiency in skin could be improved by using a specific combination of High Voltage and Low Voltage pulses.

The present invention relates to methods for transferring a nucleic acid in vivo into skin cells wherein the nucleic acid is injected by intradermal (ID) injection and is electrically transferred into skin cells with a single pulse of a High Voltage, followed by a single pulse of Low Voltage.

The invention relates to the use of a nucleic acid for the preparation of a pharmaceutical composition or medicament intended to be transferred in vivo into skin cells, wherein the pharmaceutical composition is injected by intradermal injection, and is electrically transferred into skin cells as follows:

first with a single pulse of High Voltage field strength of 1000 to 1500 V/cm and of duration of 10 µs to 1000 µs;

second, preferably after a defined lag time, with a single pulse of Low Voltage field strength of 50 to 250 V/cm and of duration of between 300 and 800 ms.

An object of the present invention is thus also a method of treatment of a human or an animal, comprising intradermally injecting a nucleic acid that encodes a therapeutically active or immunogenic molecule, and electrically permeabilizing the skin as follows:

first with a single pulse of High Voltage field strength of between 1000 and 1500 V/cm and of duration of 10 µs to 1000 µs.

second, preferably after a defined lag time, with a single pulse of Low Voltage field strength of between 50 and 250 V/cm and of duration of between 300 and 800 ms.

the nucleic acid being transferred into the tissue cells by the mean of these electric pulses.

The invention is particularly useful in the field of vaccination. Skin tissues indeed allow i) a perfect match between the vaccination site and the location of antigen-presenting cells (APCs), and ii) a reduction of antigenic doses.

In a preferred embodiment, the nucleic acid thus advantageously encodes an antigenic or immunogenic protein, such as a tumor antigen, or a viral or bacterial antigen.

In a preferred embodiment, the invention is used in the field of antitumor vaccination. The nucleic acid then advantageously encodes an antigenic protein, e.g. a tumor antigen, that is efficient for reducing, preventing or suppressing a tumor.

The invention provides a nucleic acid encoding a protein, for use in vaccination or gene therapy in subject, wherein the nucleic acid is to be administered by intradermal injection and electrical permeabilization of skin cells with:

a single pulse of High Voltage field strength of 1000 to 1500 V/cm and of duration of 10 µs to 1000 µs;

followed, preferably after a defined lag time, by a single pulse of Low Voltage field strength of 50 to 250 V/cm and of duration of between 300 and 800 ms.

LEGENDS TO THE FIGURES

FIG. 1 is a schematic representation of INVAC-1 plasmid DNA vector. Bases 1-3478: NTC8685-eRNA41H-HindIII-XbaI vector (NTC); Bases 3479-3484: HindIII cloning site (NTC/Invectys); Bases 3485-6967: Ubi-Telomerase transgene (Invectys); Bases 6968-6973: XbaI cloning site (Invectys/NTC); Bases 6974-7120: NTC8685-eRNA41H-HindIII-XbaI vector (NTC).

Figure 2:
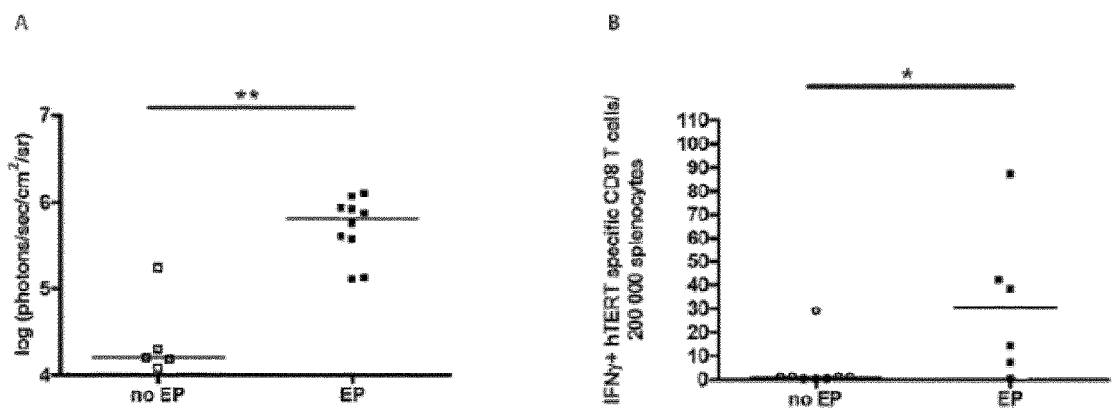

FIGS. 2A and 2B are graphs that show that electrotransfer is advantageous for gene transfer and immunization. (A) Representation of bioluminescence intensities in C57BL/6J mice after pCMV-luc injection followed or not by EP, n=5 mice for pCMV-luc ID injection alone, n=10 (from 5 mice, 2 treatments per mouse) for pCMV-luc ID injection+EP. (B) Frequency of hTERT specific INFγ+CD8 T-cell detected in C57BL/6J mice vaccinated with INVAC-1 followed or not by EP, n=6-8 mice. Bars represent median values. *=p<0.05, **=p<0.01, Mann-Whitney-Wilcoxon test.

Figure 3:
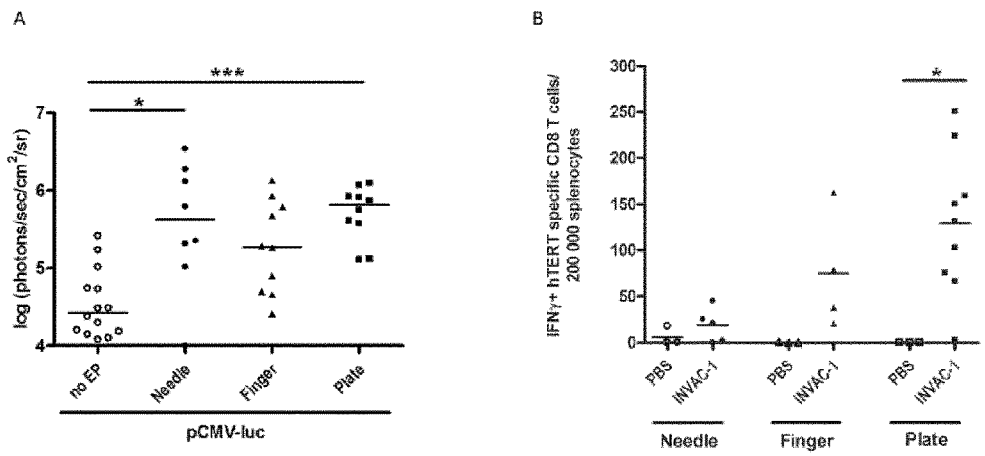

FIGS. 3A and 3B are graphs that show the choice of the best electrodes. (A) Representation of bioluminescence intensities in C57BL/6J mice after pCMV-luc electrotransfer using the three types of electrodes, n=14 mice for pCMV-luc ID injection alone, n=8-10 (from 4 to 5 mice, 2 treatments per mouse) for pCMV-luc ID injection+EP. (B) Frequency of hTERT specific INFγ+CD8 T-cell detected in HLA-B7 mice vaccinated with INVAC-1 using the three types of electrodes, n=3 mice for PBS immunization control and n=4-9 mice for INVAC-1-mediated immunization. Bars represent median values. *=p<0.05, ***=p<0.001, Kruskal-Wallis test with Dunn's multiple comparison test.

Figure 4:
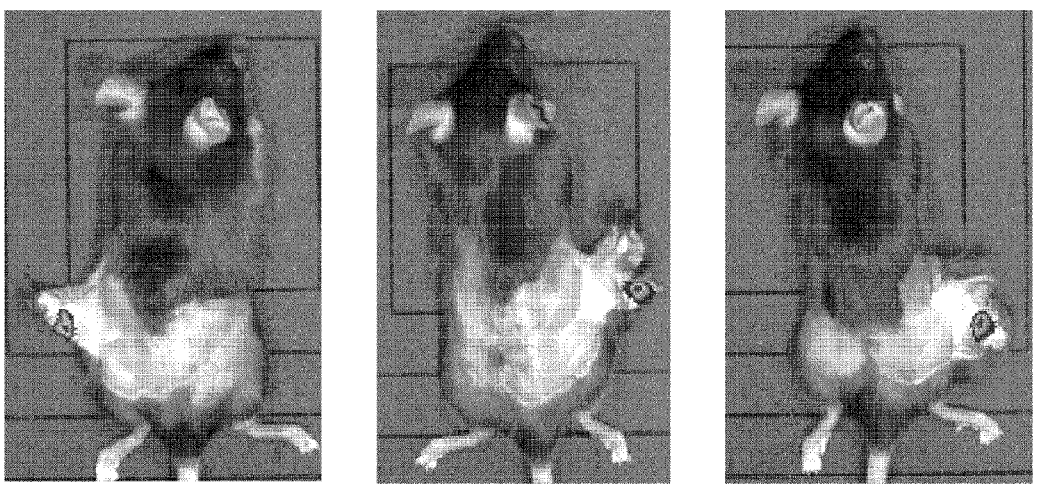

FIG. 4 is a set of photographs showing localization of luciferase gene expression in C57BL/6J mice after ID injection and electrotransfer of pCMV-luc using plate electrodes.

Figure 5:
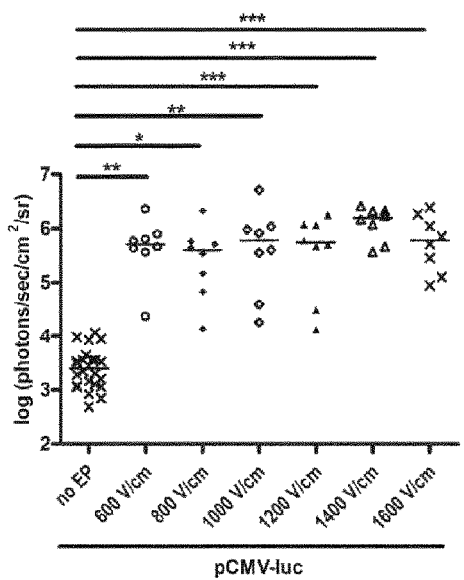

FIG. 5 is a graph that shows determination of the optimal HV pulse intensity in C57BL/6J mice for intradermally injected pCMV-luc electrotransfer using plate electrodes, n=24 mice for pCMV-luc ID injection alone, n=8 (from 4 mice, 2 treatments per mouse) for pCMV-luc ID injection+EP. Bars represent median values. *=p<0.05, =p<0.01, *=p<0.001, Kruskal-Wallis test with Dunn's multiple comparison test.

Figure 6:
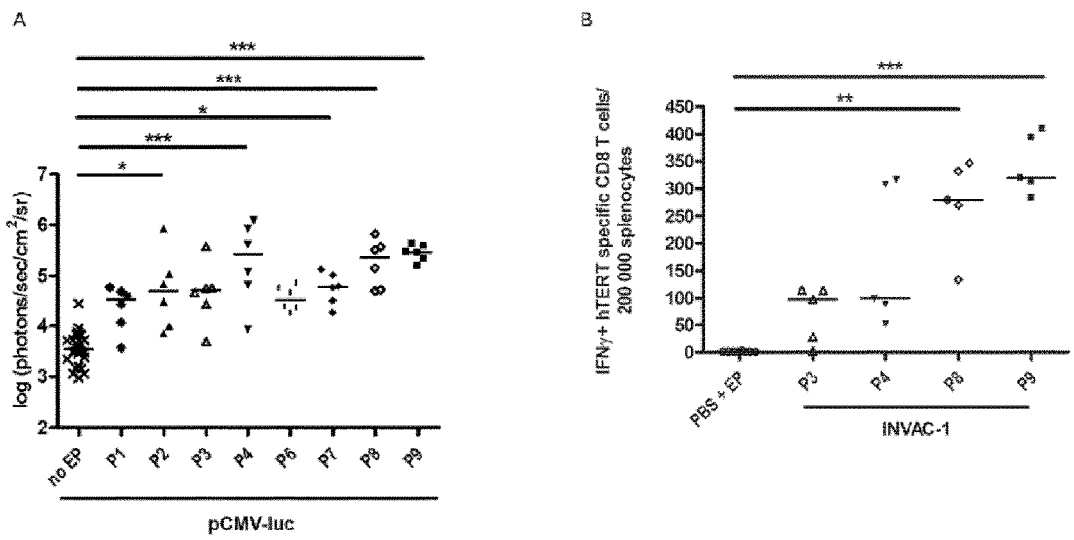

FIGS. 6A and 6B are graphs that show the choice of the best HV-LV pulses combination in C57BL/6J mice. (A) Bioluminescence obtained after pCMV-luc ID injection upon various HV-LV pulses combinations, n=30 mice for pCMV-luc ID injection alone and n=6 (from 3 mice, 2 treatments per mouse) for pCMV-luc ID injection+EP. (B) Frequency of hTERT specific IFNγ+CD8 T-cell detected in C57BL/6J mice vaccinated with INVAC-1 according to various combinations of HV-LV pulses, n=8 mice for PBS immunization control and n=5 mice for INVAC-1-mediated immunization. Bars represent median values. *=p<0.05, =p<0.01, *=p<0.001, Kruskal-Wallis test with Dunn's multiple comparison test.

DETAILED DESCRIPTION OF THE INVENTION

Definitions

The term HV means High Voltage, and the term LV means Low Voltage.

As used herein, the term "skin" denotes the skin of an animal, for instance a human, or a non-human mammal such as a rodent (e.g. a mouse, a rabbit or a rat), a dog, a cat, or a primate, horse, a goat, a pig, a sheep, a cow etc. In a preferred embodiment, the nucleic acid is transferred into cells of the dermis. The skin cells, into which the nucleic acid is transferred according to the invention, are preferably dendritic cells, but may also include keratinocytes, melanocytes, fibroblasts, or myeloid or lymphoid cells. The term "nucleic acid" means any nucleic acid of interest, in particular any nucleic acid capable of expressing a protein of interest. The nucleic acid can be single-stranded or double-stranded DNA or RNA (e.g. antisense or iRNA). Preferably it is DNA, preferably double-stranded DNA. In a preferred embodiment, the nucleic acid is a DNA expression vector of the type well known in the art. Generally, an expression vector contains a promoter operably linked to a DNA sequence that encodes the protein of interest.

The term "TERT" refers to "Telomerase Reverse Transcriptase", which is the major determinant of telomerase activity, including wild-type telomerase, or variants thereof.

The term "immunogenic" means that the composition or construct to which it refers is capable of inducing an immune response upon administration "Immune response" in a subject refers to the development of an innate and adaptative immune response, including a humoral immune response, a cellular immune response, or both, to an antigen. A "humoral immune response" refers to one that is mediated by antibodies. A "cellular immune response" is one mediated by T-lymphocytes. It includes the production of cytokines, chemokines and similar molecules produced by activated T-cells, white blood cells, or both Immune responses can be determined using standard immunoassays and neutralization assays for detection of the humoral immune response, which are known in the art. In the context of anticancer vaccination, the immune response preferably encompasses stimulation or proliferation of cytotoxic CD8 T-cells and/or CD4 T-cells and can be determined using immunoassays such as the ELISpot assay, the in vivo cytotoxicity assay or the cytokine secretion binding assay.

As used herein, the term "treatment" or "therapy" or "immunotherapy" refers to any of the alleviation, amelioration and/or elimination, reduction and/or stabilization (e.g., failure to progress to more advanced stages) of a symptom, as well as delay in progression of the disease, or of a symptom thereof. When the disease is cancer, the term thus includes achievement of an efficient antitumoral immune response observed in cancer patients.

As used herein, the term "prevention" or "preventing" refers to the alleviation, amelioration and/or elimination, reduction and/or stabilization (e.g., failure to progress to more advanced stages) of a prodrome, i.e. any alteration or early symptom (or set of symptoms) that might indicate the start of a disease before specific symptoms occur.

The "patient" or "subject" is typically a mammal subject, such as listed above, preferably a human subject, of any age, sex, or severity of the condition.

Electrotransfer Parameters

The nucleic acid is preferably intended to be brought into contact with the skin cells before applying the single LV pulse, and still more preferably, before the application of the single HV pulse. The time between injection of nucleic acid and electrical pulses, especially between injection and the single HV pulse, is not critical. Typically, the pharmaceutical composition has been brought into contact with the skin cells from few seconds to 10 minutes, e.g. from 30 seconds to 5 minutes. An interval of 5 to 10 minutes before the HV pulse is also acceptable. The nucleic acid or pharmaceutical composition containing the nucleic acid is brought into contact with the skin cells (i.e. the dermis cells) by intradermal injection.

In an advantageous aspect of the invention, the single pulse of High Voltage preferably has a field strength of between 1100 and 1400 V/cm, preferably of 1250 V/cm.

The single pulse of High Voltage may have a duration of between 50 and 150 µs, preferably of 100 µs.

In an advantageous aspect of the invention, the single pulse of Low Voltage preferably has a field strength of between 100 and 200 V/cm, preferably of 180 V/cm.

The single pulse of Low Voltage may preferably have a duration of between 350 and 600 ms, still preferably 400 ms.

In a preferred embodiment, the single pulse of High Voltage preferably has a field strength of between 1100 and 1400 V/cm, preferably of 1250 V/cm, and a duration of between 50 and 150 µs, preferably of 100 µs, and the single pulse of Low Voltage has a field strength of between 100 and 200 V/cm, preferably of 180 V/cm, and a duration of between 350 and 600 ms, still preferably 400 ms.

In a particular embodiment, when the subject is a human subject, the single pulse of High Voltage may have a field strength of 1250 V/cm, and preferably a duration of 100 µs, and the single pulse of Low Voltage may have a field strength of 180 V/cm, and preferably a duration of 400 ms.

The LV pulse may be of the same polarity or of an opposite polarity than the HV pulse.

Preferably, the single LV pulse is a squared pulse. It can also be trapezoidal, or discontinous.

The single HV pulse may be advantageously a squared pulse.

The HV and LV pulses may be separated by a lag and this lag can advantageously be of between 300 and 3000 ms, preferably between 500 and 1200 ms, typically of 1000 ms.

An object of the invention is the electroporation method itself, comprising placing electrodes near the dermis cells containing the nucleic acid interstitially, then electrically permeabilizing the dermis cells as follows:
- first with a single pulse of High Voltage field strength of between 1000 and 1500 V/cm and of duration of 10 µs to 1000 µs.
- second, preferably after a defined lag time, with a single pulse of Low Voltage field strength of between 50 and 250 V/cm and of duration of between 300 and 800 ms.
- the nucleic acid being transferred into the dermis cells by result of these electric pulses.

A programmable voltage generator can be used.

The electrodes to be used may be invasive needle electrodes (such as N-30-4B, IGEA), that may typically consist in two rows of four long needles, 4 mm apart, or invasive finger electrodes (such as F-05-OR, IGEA) that may typically consist in two rows of three short needles, 4 mm apart, but are preferably non-invasive plate electrodes (such as P30-8B, IGEA).

The electrodes are to be positioned at the vicinity of the injection site such that electrical field between the electrodes passes through the injection site or region wherein the injected liquid has diffused upon injection. A conductive gel may be advantageously used, as known by the skilled person.

In a particular embodiment, the electrodes may be carried by a device making both the injection and the electrical stimulation.

Genetic Constructs, Immunogenic Compositions Preferably, the nucleic acid is a genetic construct comprising a polynucleotide sequence encoding a protein of interest, and regulatory sequences (such as a suitable promoter(s), enhancer(s), terminator(s), etc.) allowing the expression (e.g. transcription and translation) of the protein product in the host cell or host organism.

The genetic constructs of the invention may typically be in a form suitable for transformation of the intended host cell or host organism, in a form suitable for integration into the genomic DNA of the intended host cell or in a form suitable for independent replication, maintenance and/or inheritance in the intended cell or organism. For instance, the genetic constructs of the invention may be in the form of a vector, such as for example a plasmid, cosmid, YAC, a viral vector or transposon. In particular, the vector may be an expression vector, i.e. a vector that can provide for transcription of RNAs and/or expression of proteins in vivo, especially in cells of dermis.

In a preferred but non-limiting aspect, a genetic construct of the invention comprises i) at least one nucleic acid encoding a protein of interest; operably connected to ii) one or more regulatory elements, such as a promoter and optionally a suitable terminator; and optionally also iii) one or more further elements of genetic constructs such as 3'- or 5'-UTR sequences, leader sequences, selection markers, expression markers/reporter genes, and/or elements that may facilitate or increase (the efficiency of) transformation or integration.

It will be appreciated that the use according to the invention encompasses the case where two or more nucleic acids able to express in vivo different active molecules are used to prepare the pharmaceutical composition. The nucleic acids are chosen so as to be complementary and/or act in synergistic way in treating a condition. In that case, the nucleotide sequences encoding the different molecules may be under the control of the same promoter or different promoters. Compositions can be prepared, comprising said nucleic acid(s) or vector(s). In one embodiment, the compositions are immunogenic. They can comprise a carrier or excipients that are suitable for administration in humans or mammals (i.e. non-toxic). Such excipients include liquid, semisolid, or solid diluents that serve as pharmaceutical vehicles, isotonic agents, stabilizers, or any adjuvant.

Non-Coding Nucleic Acids

In another embodiment, the nucleic acid does not encode any protein of interest, but inhibits or diminishes the expression of a target gene. For instance, the nucleic acid may be an antisense or an interferent RNA. Nucleic acids may be natural RNA nucleic acid molecules or nucleic acid-analogs like PLNAs. In particular, the nucleic acid may be small interference RNA (siRNAs), e.g. single-stranded or double-stranded RNA, such as a short single-stranded or double-stranded RNA from about 17 nucleotides to about 29 nucleotides in length, preferably from about 19 to about 25 nucleotides in length, that are targeted to the target mRNA. In case of double-stranded RNA, such siRNA comprises a sense RNA strand and a complementary antisense RNA strand annealed together.

Vaccination and/or Gene Therapy

In a particular embodiment, the nucleic acid is useful in gene therapy and/or in vaccination, through expression of a protein of interest. In a preferred embodiment, the protein of interest has an immunostimulating action, still preferably a vaccinal effect. Advantageously, a humoral immune response is obtained.

In a preferred aspect, the nucleic acid comprises nucleic acid sequences able to express in vivo in the transfected skin cells one or more therapeutically active molecule(s), preferably a protein or proteins of interest.

This active molecule or protein of interest may act in the skin itself and/or outside the skin in another location within the body, for example on a tumor located anywhere in the body if the expressed molecule is active as an anti-tumor vaccine, or an infection located anywhere in the body if the expressed molecule is active as an anti-infectious vaccine.

An example of a therapeutic molecule of interest includes a TERT protein, useful as an anti-tumor vaccine. It will be appreciated that there is no limitation to the kind of molecules that can be expressed in accordance with the invention and therefore the one skilled in the art will be able to carry out the invention with a molecule of interest knowing the coding sequence thereof and routine experimentation to select the best construction or expression vector.

In an interesting aspect, as a therapeutically active molecule, the nucleic acid encodes one or several immunogens (or immunogenic peptides, polypeptides or proteins, including glycoproteins) that are able to induce an immune response in the host. In one embodiment, the immune response is a protective immune response for the host. In this embodiment, the invention relates to producing an immunogenic composition or a prophylactic or a therapeutic vaccine, that is directed against cancers, or against a microorganism, e.g. virus or bacteria.

By way of example only, the nucleic acid encodes one or several immunogens of HIV, HBV, Epstein-Barr virus, pseudorabies virus, syncitia forming virus, oncovirus, papilloma virus, etc. The person skilled in the art has access to the nucleic acids encoding the most interesting molecules for the chosen application, for example to the most efficient immunogens or combinations of immunogens for a particular disease.

In another embodiment, the immune response leads to the production of antibodies, especially polyclonal antibodies, and these antibodies are intended to be recovered from the produced serum and used in an usual manner.

In still another embodiment, the nucleic acid encodes an antigenic peptide or protein that, upon administration to the subject, e.g. a mouse, triggers the production of specific antibodies.

Treatment of Tumors

In a particular embodiment, a method for preventing or treating a tumor or undesired proliferation of cells (e.g. a dysplasia) in a patient is described, which method comprises administering an effective amount of nucleic acid or immunogenic composition in a patient in need thereof, using the electroporation method of the invention. Said nucleic acid or immunogenic composition is administered in an amount sufficient to induce an immune response in the patient.

The tumor may be any undesired proliferation of cells, in particular a benign tumor or a malignant tumor, especially a cancer.

The cancer may be at any stage of development, including the metastatic stage.

The nucleic acid thus preferably expresses one or several active molecule(s) selected so that the pharmaceutical composition is efficient in reducing, suppressing or regressing tumor angiogenesis, or reduces or suppress tumor growth, or inhibits metastasis. As an example, a nucleic encoding a tumor antigen (e.g. TERT) can be used.

In a particular embodiment, the tumor is a solid cancer, a sarcoma or a carcinoma. In particular the tumor may be selected from the group consisting of melanoma, brain tumor such as glioblastoma, neuroblastoma and astrocytoma and carcinomas of the bladder, breast, cervix, colon, lung, especially non-small cell lung cancer (NSCLC), pancreas, prostate, head and neck cancer, or stomach cancer.

In another embodiment, the tumor may be a liquid tumor, e.g. a hematopoietic tumor, lymphoma or leukemia, such as a lymphocytic leukemia, myeloid leukemia, lymphoma including Hodgkin's disease, multiple myeloma, malignant myeloma.

While it will be understood that the amount of material needed will depend on the immunogenicity of each individual construct and cannot be predicted a priori, the process of determining the appropriate dosage for any given construct is straightforward. Specifically, a series of dosages of increasing size, starting at about 5 to 30 µg, or preferably 20-25 µg, up to about 500-1000 µg for instance, is administered to the corresponding species and the resulting immune response is observed, for example by detecting the cellular immune response by an IFNγ ELISpot assay (as described in the experimental section), by detecting cytotoxic T lymphocyte (CTL) responses using an in vivo lysis assay a chromium release assay or detecting TH (helper T cell) response using a cytokine release assay.

In a preferred embodiment, the vaccination regimen comprises one to three injections, preferably repeated three or four weeks later. In a particular embodiment, the vaccination schedule can be composed of one or two injections followed three or four weeks later by at least one cycle of three to five injections. In another embodiment, a primer dose consists of one to three injections, followed by at least a booster dose every year, or every two or years for instance. These are examples only, and any other vaccination regimen is herein encompassed.

The present invention is described in further details with the presentation of the following non-limitative experiments.

EXAMPLES

Gene Electrotransfer Procedure for Antitumor Vaccination

In the present study, a gene electrotransfer procedure into the dermis for vaccination purposes against the telomerase tumor antigen has been optimized. In a first assessment, the luciferase reporter gene was used to evaluate gene electrotransfer efficiency into the dermis as a function of the parameters used. In a second time, these parameters were tested for their efficiency in immunizing mice against telomerase epitopes. Different types of electrodes were used, either non-invasive or invasive, as well as a range of various applied electric fields.

Two important read-outs were assessed which were first the intensity of luciferase expression at the site of electrotransfer and secondly the intensity of vaccine specific interferon γ (IFNγ) positive CD8 T-cells, which is the kind of immune response expected for anti-cancer vaccines (Vesely et al., 2011). Three major electrotransfer factors were investigated: the electrode types and the impact of the HV and LV pulses.

Materials and Methods

Mice

HLA-B7 mice are transgenic mice expressing the HLA-B*0702 class I molecule. They are knock-out for mouse class I $H2D^b$ and $H2K^b$ molecules. They were previously described by Rohrlich et al. 2003, and were obtained from The Pasteur Institute internal breeding. Female C57BL/6J mice (6-8 week old) were purchased from Janvier (Saint-Berthevin, France) or Harlan (Gannat, France) laboratories.

Animals were housed at specific pathogen-free animal facilities of the Pasteur Institute or Gustave Roussy Institute. All animal experiments were performed in strict compliance with the ethical guidelines issued by the European Committee (Directive 2010/63/EU) and animals were handled in strict accordance with good animal practice.

Plasmids pCMV-luc (PF461, Plasmid Factory, Bielefeld, Germany) is a double stranded plasmid DNA of 6233 by encoding the firefly luciferase reporter gene placed under the control of the cytomegalovirus promoter (pCMV).

INVAC-1 is a double stranded plasmid DNA of 7120 by encoding a modified sequence of the telomerase protein fused to the Ubiquitin protein sequence. The encoded telomerase protein is enzymatically inactive but can still induce immune responses against telomerase epitopes in vivo. The ubiquitin-telomerase insert is cloned into the NTC8685-ERNA41H-HindIII-XbaI expression vector designed by Nature Technology Corporation (Lincoln, Nebr.). The presence of the ubiquitin increases the addressing of the Telomerase Reverse Transcriptase (TERT) protein to the proteasome and increases the MHC class I presentation pathway of TERT-derived peptides (Rodriguez et al., 1997; Wang et al., 2012). The DNA sequence coding for the TERT protein was deleted of 47 amino-acids in the N-terminal region, which includes the nucleolar localization signal. Moreover, 3 amino-acids were removed inside the catalytic site of TERT (VDD) to abolish the protein enzymatic activity. INVAC-1 plasmid was stored at −20° C., in phosphate buffered saline (PBS), at a concentration of 2 mg/mL prior use. FIG. 1 represents INVAC-1 plasmid map.

EP Generator and Electrodes

Gene electrotransfer was performed using the Cliniporator® (IGEA, Carpi, Italy) delivering HV pulses and LV pulses. Voltages were set up according to the distance between the 2 rows of the electrodes. Different types of electrodes were used: (1) invasive needle electrodes (N-30-4B, IGEA) consisting in 2 rows of 4 long needles, 4 mm apart, (2) invasive finger electrodes (F-05-OR, IGEA) consisting in 2 rows of 3 short needles, 4 mm apart, (3) non-invasive plate electrodes (P30-8B, IGEA) consisting in 2 metallic plates, 1 mm thick and 5 mm apart.

In Vivo Gene Electrotransfer

Mice were anesthetized prior to intradermal (ID) injections, either with 2% isoflurane/oxygen mixture gas anesthesia (Abbot, Suresnes, France) or with a mix solution (intraperitoneal route) of 2% xylazine (Rompun, Bayer Santé, Loos, France) and 8% ketamine (Imalgen 1000, Merial, Lyon, France) in PBS according to individual animal weight. ID injection was performed on the lower part of the flank (bilateral injections) with 29 G insulin specific needles after shaving. Each animal, either from HLA-B7 or C57BL/6J mouse strain received a single dose of DNA, corresponding to 100 µg of INVAC-1 plasmid (50 µg in 25 µL PBS per flank) or 10 µg of pCMV-luc plasmid (5 µg in 25 µL PBS per flank).

Immediately after ID injection, gene electrotransfer was performed using one HV pulse (100 µs duration) followed 1000 ms later by one LV pulse (400 ms duration). Electrodes were placed in such a way they surrounded the bleb formed by the plasmid injection. Both finger or needle electrodes were pressed for about 5 mm into the skin. Conductive gel (Labo FH, gel de contact bleu, NM Médical, France) was used for the plate electrodes in order to improve the contact between the metallic plates and the skin.

In Vivo Bioluminescence Imaging and Electrotransfer Localization

Two days after pCMV-luc electrotransfer, C57BL/6J mice were injected intraperitoneally with 0.15 mg of beetle luciferin (Promega, Lyon, France) per gram of body mass. Twenty minutes after the injection, animals were anesthetized using a 2% isoflurane/oxygen mixture gas anesthesia and the luciferase-driven biochemoluminescent reaction was detected using the In Vivo Imaging System IVIS 50 (Xenogen, Waltham, USA). In order to validate the electrogenetransfer in the skin, 3 mice were killed by cervical dislocation 20 minutes after luciferin injection and the electropermeabilized skin area was removed from the animals. Bioluminescence intensities were assessed in the skin flap and in the underlying muscles.

Splenocytes Preparation

Fourteen days after ID INVAC-1 injection and electrotransfer, mice were sacrificed by cervical dislocation and spleens were recovered. Under sterile conditions, each spleen was pressed through a 70 μm nylon mesh (cell strainer, BD Falcon Franklin Lakes, USA) and washed with complete RPMI culture medium (Roswell Park Memorial Institute medium supplemented with 10% heat-inactivated Fetal Calf Serum (FCS), 1% sodium-pyruvate, 1% penicillin-streptomycin and 0.1% β-mercaptoethanol). All components were purchased from Life technologies SAS (Saint-Aubin, France). Splenocytes were purified on a Ficoll gradient (Lymphocyte Separation Medium, Eurobio, Courtaboeuf, France), washed and counted using the Cellometer® Auto T4 Plus counter (Ozyme, Saint-Quentin-en-Yvelines, France) and adjusted at 2 million cells/mL in complete RPMI before being used in the IFNγ ELISpot assay.

HLA-B7 and H2 Restricted Peptides

Human TERT (hTERT) peptides restricted to HLA-B*0702 class I molecule have been previously described (Adotevi et al., 2006; Cortez-Gonzalez et al., 2006). Other peptides were predicted by in-silico epitope prediction in order to bind mouse MHC class I, $H2K^b$, $H2D^b$ using four algorithms available online: Syfpeithi (http://www.syfpeithi.de/), Bimas (http://www-bimas.cit.nih.gov), NetMHCpan and SMM (http://tools.immuneepitope.org/main/). All synthetic peptides were purchased lyophilized (>90% purity) from Proimmune (Oxford, UK). Lyophilized peptides were dissolved in sterile water at 2 mg/mL and stored in 35 μL aliquots at −20° C. prior use. Details of peptides sequence according to B7 or H2 restriction are shown below:

H2 Restricted hTERT Peptides:
$H2D^b$: RPIVNMDYV (p660).
$H2K^b$: HAQCPYGVL (p429)
HLA-B7 Restricted hTERT Peptides:
HLA-B7: RPSLTGARRL (p351)
HLA-B7: RPAEEATSL (p277)
HLA-B7: LPSDFKTIL (p1123)

IFNγ ELISpot Assay

Briefly, polyvinylidine fluoride microplates (IFNγ ELISpot kit, 10×96 tests, Diaclone, Eurobio) were coated overnight with capture antibody (anti-mouse IFNγ) and blocked with sterile PBS 2% milk for 2 hours. ELISpot plates were washed and splenocytes suspensions were plated in triplicates at $2\times10^5$ cells/well. Cells were then stimulated with 5 μg/mL H2 or B7 relevant peptides or with 10 μg/mL phorbol 12-myristate 13-acetate (PMA)-ionomycine or mock stimulated with serum-free culture medium. Plates were incubated at 37° C., 5% CO2. After 19 hours, spots were revealed with a biotin-conjugated IFNγ detection antibody followed by Streptavidin-Alkaline Phosphatase and a 5-bromo-4-chloro-3'-indolyphosphate p-toluidine salt/nitroblue tetrazolium chloride (BCIP/NBT) substrate solution. Spots were counted using the Immunospot ELISpot counter and software (Cellular Technology Limited, Bonn, Germany).

Statistical Analysis and Data Handling

Prism-5 software was used for data handling, analysis and graphic representations. For statistical analyses of bioluminescence and ELISpot assays, either a Mann-Whitney-Wilcoxon test or a Kruskall-Wallis test with Dunn's multiple comparison test was used, depending on the experiment. Significance was set at p-value<0.05.

Results

Electrotransfer Achieves Optimal In Vivo Transgene Expression and the Induction of Antigen Specific CD8 T-Cells Either pCMV-luc or INVAC-1 plasmids were intradermally injected into shaved C57BL/6J mice flanks, followed or not by the application of EP (1 HV pulse at 1000 V/cm during 100 μs followed 1000 ms later by 1 LV pulse at 140 V/cm during 400 ms). No erythema was observed after shaving, nor during and after the electrotransfer procedure. Two parameters were measured after gene electrotransfer: the luciferase expression after ID electrotransfer with pCMV-luc and the frequency of the IFNγ secreting hTERT specific CD8 T-cells after ID electrotransfer of INVAC-1. Both luciferase expression (FIG. 2A) and frequency of the IFNγ secreting hTERT specific CD8 T-cells (FIG. 2B) were significantly increased when EP were applied directly after DNA injection (p<0.01 and p<0.05, respectively) in comparison with animals which received DNA injection alone without electrotransfer. Thus, electrotransfer induces significant levels of hTERT specific CD8 T-cell responses after ID vaccination with INVAC-1 and significant levels of luciferase expression after ID injection of pCMV-luc.

Choice of the Best Electrodes for Optimal Gene Transfer and Generation of Intense Cellular Immune Responses Different types of electrodes can be used for in vivo electrotransfer in the skin (Gothelf & Gehl, 2010). Therefore three different electrodes (plate electrodes, finger electrodes and needle electrodes, as described in the Materials and Methods section) were tested in order to determine which one was best suited for efficient gene transfer and the generation of intense specific cellular immune responses in mice. Results showed that the three types of electrodes enhanced significantly the electrotransfer of the pCMV-luc plasmid in C57BL/6J mice as compared to the animals which received the plasmid with no EP (FIG. 3A). However, there was a better homogeneity in the response for the group of mice electrotransferred with plate electrodes (p<0.001). To a lesser extent, animals electrotransferred with needle electrodes also presented significant levels of luciferase expression (p<0.05).

Similar results were obtained from immunogenicity studies in HLA-B7 mice. When mice were intradermally vaccinated with INVAC-1 followed by skin electrotransfer, the highest median frequency of IFNγ+ specific CD8 T-cells was detected when plate electrodes were used and this difference was statistically significant in comparison with the PBS control group (p<0.05) (FIG. 3B).

In summary, plate electrodes displayed both the best ability to electrotransfer pCMV-luc and to generate significant levels of hTERT specific CD8 T-cells.

Localization of Luciferase after ID Injection Followed by Gene Electrotransfer

Gene electrotransfer is known to be very efficient in muscles (Andre et al., 2008). In order to make sure that luciferase gene was only electrotransferred into the skin after an ID injection of pCMV-luc, a flap skin was opened in the flank of C57BL/6J mice at the site of the treatment and the bioluminescence for both the skin flap and for the underlying muscles was measured four days after gene electrotransfer. Plate electrodes were used for this gene electrotransfer study. The inventors confirmed that transgene expression occurred only in the skin and that no expression was detected in the underlying muscles (FIG. 4).

Choice of the HV Pulse

The first optimization of the electrical parameters consisted in determining the most efficient amplitude of the HV pulse (100 µs duration) among the following field amplitudes: 600, 800, 1000, 1200, 1400, 1600 V/cm. The intensity of the LV pulse (400 ms duration) was kept constant at 140 V/cm and the lag between HV and LV pulses was set up at 1000 ms. This evaluation was performed using the luciferase reporter gene and C57BL/6J mice.

C57BL/6J mice electrotransferred at 1200 V/cm, 1400 V/cm and 1600 V/cm presented the most significant enhancement of luciferase expression as compared to control mice ($p<0.001$) (FIG. 5). In particular, the highest median bioluminescence was obtained in the group treated at 1400 V/cm and there was also a better homogeneity in the results for this group as compared to other groups. However, there was no statistical difference between responses obtained from these three groups, i.e. 1200, 1400 and 1600 V/cm.

Choice of the Best HV-LV Pulses Combination

The influence of HV-LV combinations was evaluated on both pCMV-luc electrotransfer and on INVAC-1 induced specific cellular immune responses after ID injection into C57BL/6J mice's skin. Regarding the HV pulse, 1000 V/cm or 1400 V/cm were chosen to be combined with various LV pulses. Directly after ID injection of pCMV-luc or INVAC-1, one HV pulse (100 µs duration) at 1000 V/cm or 1400 V/cm was applied followed by one LV pulse (400 ms duration) at either 60 V/cm, 100 V/cm, 140 V/cm, 180 V/cm or 220 V/cm. The ten HV-LV pulses combinations were referred to as "P1" to "P10" (Table 1).

TABLE 1

Combinations of HV-LV pulses evaluated in bioluminescence and in ELISpot assays.

| (V/cm) | LV = 60 | LV = 100 | LV = 140 | LV = 180 | LV = 220 |
|---|---|---|---|---|---|
| HV = 1000 | P1 | P2 | P3 | P4 | P5 |
| HV = 1400 | P6 | P7 | P8 | P9 | P10 |

Due to technical limitations, the Cliniporator® was not able to deliver constantly 220 V/cm during 400 ms. Thus, results obtained when P5 and P10 conditions were used did not generate reliable data and were excluded for data analyses.

The 3 combinations of HV-LV pulses that generated the highest median bioluminescence intensities were P4, P8 and P9 (FIG. 6A). All of these 3 combinations displayed very high statistical differences when compared to pCMV-luc injection alone without EP ($p<0.001$). In particular, P9 showed the best median bioluminescence intensity, the highest value for the minimum bioluminescence intensity and the lowest point dispersion.

P4, P8 and P9 HV-LV pulses combinations were then tested for ID vaccination with INVAC-1. The intensities of hTERT specific CD8 T-cell responses of these groups were compared with the P3 combination which was previously published for DNA electrotransfer into the subcutaneous tissue (Andre et al., 2008). When analyzing the data from the immunogenicity assay, P8 and P9 combinations appeared to be the best ones, allowing the generation of significant frequencies of IFNγ+ specific CD8 T-cells in comparison with control mice ($p<0.01$ and $p<0.001$, respectively) (FIG. 6B). Even though the difference between P8 and P9 groups was not statistically significant, P9 displayed a higher median frequency of hTERT specific CD8 T-cells.

Given bioluminescence and immunogenicity data analyses, the best HV-LV pulses combination appeared to be P9, i.e. one HV pulse (100 µs duration) at 1400 V/cm followed by one LV pulse (400 ms duration) at 180 V/cm.

Conclusion

In this study, the procedure for both in vivo luciferase gene electrotransfer into the dermis and telomerase-based ID vaccination was optimized Non-invasive plate electrodes delivering one high voltage pulse of 100 µs followed by one low voltage pulse of 400 ms displayed both the highest level of luciferase expression and the highest number of telomerase specific CD8 T-cells. The results generated with this telomerase DNA vaccine can set up a global DNA vaccination procedure using the electrotransfer technology independently of the antigen, should it be a tumor antigen, or a viral or bacterial antigen.

REFERENCES

Adotevi O, Mollier K, Neuveut C, Cardinaud S, Boulanger E, et al. (2006) Immunogenic HLA-B*0702-restricted epitopes derived from human telomerase reverse transcriptase that elicit antitumor cytotoxic T-cell responses. Clin Cancer Res 12: 3158-3167.

Anderson E D, Mourich D V, Fahrenkrug S C, LaPatra S, Shepherd J, et al. (1996) Genetic immunization of rainbow trout (Oncorhynchus mykiss) against infectious hematopoietic necrosis virus. Mol Mar Biol Biotechnol 5: 114-122.

Andre F M, Gehl J, Sersa G, Preat V, Hojman P, et al. (2008) Efficiency of high- and low-voltage pulse combinations for gene electrotransfer in muscle, liver, tumor, and skin. Hum Gene Ther 19: 1261-1271.

Andre F M, Mir L M (2010) Nucleic Acids Electrotransfer In Vivo: Mechanisms and Practical Aspects. Current Gene Therapy 10: 267-280.

Barry M A, Lai W C, Johnston S A (1995) Protection against mycoplasma infection using expression-library immunization. Nature 377: 632-635.

Bei R, Scardino A (2010) TAA polyepitope DNA-based vaccines: a potential tool for cancer therapy. J Biomed Biotechnol 2010: 102758.

Bergman P J, McKnight J, Novosad A, Charney S, Farrelly J, et al. (2003) Long-term survival of dogs with advanced malignant melanoma after DNA vaccination with xenogeneic human tyrosinase: a phase I trial. Clin Cancer Res 9: 1284-1290.

Breton M, Mir L M (2011) Microsecond and nanosecond electric pulses in cancer treatments. Bioelectromagnetics.

Cortez-Gonzalez X, Sidney J, Adotevi O, Sette A, Millard F, et al. (2006) Immunogenic HLA-B7-restricted peptides of hTRT. Int Immunol 18: 1707-1718.

Dolter K E, Evans C F, Ellefsen B, Song J, Boente-Carrera M, et al. (2011) Immunogenicity, safety, biodistribution and persistence of ADVAX, a prophylactic DNA vaccine for HIV-1, delivered by in vivo electroporation. Vaccine 29: 795-803.

Escoffre J M, Portet T, Wasungu L, Teissie J, Dean D, et al. (2009) What is (still not) known of the mechanism by which electroporation mediates gene transfer and expression in cells and tissues. Mol Biotechnol 41: 286-295.

Favard C, Dean D S, Rols M P (2007) Electrotransfer as a non viral method of gene delivery. Current Gene Therapy 7: 67-77.

Fioretti D, Iurescia S, Fazio V M, Rinaldi M (2013) In vivo DNA electrotransfer for immunotherapy of cancer and neurodegenerative diseases. Curr Drug Metab 14: 279-290.

Gothelf A, Gehl J (2010) Gene electrotransfer to skin; review of existing literature and clinical perspectives. Curr Gene Ther 10: 287-299.

Gothelf A, Gehl J (2012) What you always needed to know about electroporation based DNA vaccines. Hum Vaccin Immunother 8: 1694-1702.

Keir M E, Butte M J, Freeman G J, Sharpe A H (2008) PD-1 and its ligands in tolerance and immunity. Annu Rev Immunol 26: 677-704.

Kirman J R, Seder R A (2003) DNA vaccination: the answer to stable, protective T-cell memory? Curr Opin Immunol 15: 471-476.

Kolar P, Knieke K, Hegel J K E, Quandt D, Burmester G R, et al. (2009) CTLA-4 (CD152) Controls Homeostasis and Suppressive Capacity of Regulatory T Cells in Mice. Arthritis and Rheumatism 60: 123-132.

Lee A H, Suh Y S, Sung J H, Yang S H, Sung Y C (1997) Comparison of various expression plasmids for the induction of immune response by DNA immunization. Mol Cells 7: 495-501.

Li L, Saade F, Petrovsky N (2012) The future of human DNA vaccines. J Biotechnol 162: 171-182.

Lindau D, Gielen P, Kroesen M, Wesseling P, Adema G J (2013) The immunosuppressive tumour network: myeloid-derived suppressor cells, regulatory T cells and natural killer T cells. Immunology 138: 105-115.

Liu M A (2011) DNA vaccines: an historical perspective and view to the future Immunol Rev 239: 62-84.

Mir L M, Belehradek M, Domenge C, Orlowski S, Poddevin B, et al. (1991) [Electrochemotherapy, a new antitumor treatment: first clinical trial]. C R Acad Sci III 313: 613-618.

Mir L M, Moller P H, Andre F, Gehl J (2005) Electric pulse-mediated gene delivery to various animal tissues. Adv Genet 54: 83-114.

Mir L M (2006) Bases and rationale of the electrochemotherapy. Ejc Supplements 4: 38-44.

Rochard A, Scherman D, Bigey P (2011) Genetic immunization with plasmid DNA mediated by electrotransfer. Hum Gene Ther 22: 789-798.

Rodriguez F, Zhang J, Whitton J L (1997) DNA immunization: ubiquitination of a viral protein enhances cytotoxic T-lymphocyte induction and antiviral protection but abrogates antibody induction. J Virol 71: 8497-8503.

Rohrlich P S, Cardinaud S, Firat H, Lamari M, Briand P, et al. (2003) HLA-B*0702 transgenic, H-2KbDb double-knockout mice: phenotypical and functional characterization in response to influenza virus. Int Immunol 15: 765-772.

Satkauskas S, Bureau M F, Puc M, Mahfoudi A, Scherman D, et al. (2002) Mechanisms of in vivo DNA electrotransfer: Respective contributions of cell electropermeabilization and DNA electrophoresis. Molecular Therapy 5: 133-140.

Satkauskas S, Andre F, Bureau M F, Scherman D, Miklavcic D, et al. (2005) Electrophoretic component of electric pulses determines the efficacy of In Vivo DNA electrotransfer. Human Gene Therapy 16: 1194-1201.

Shevach E M (2009) Mechanisms of foxp3+ T regulatory cell-mediated suppression. Immunity 30: 636-645.

Stevenson F K, Palucka K (2010) Understanding and activating immunity against human cancer. Curr Opin Immunol 22: 212-214.

Tang D C, DeVit M, Johnston S A (1992) Genetic immunization is a simple method for eliciting an immune response. Nature 356: 152-154.

Villemejane J, Mir L M (2009) Physical methods of nucleic acid transfer: general concepts and applications. British Journal of Pharmacology 157: 207-219.

Vesely M D, Kershaw M H, Schreiber R D, Smyth M J (2011) Natural innate and adaptive immunity to cancer. Annu Rev Immunol 29: 235-271.

Wang Q, Lei C, Wan H, Liu Q (2012) Improved cellular immune response elicited by a ubiquitin-fused DNA vaccine against Mycobacterium tuberculosis. DNA Cell Biol 31: 489-495.

Wolff J A, Malone R W, Williams P, Chong W, Acsadi G, et al. (1990) Direct gene transfer into mouse muscle in vivo. Science 247: 1465-1468.

The invention claimed is:

1. An in vivo method for expressing a human Telomerase Reverse Transcriptase (hTERT) in a subject, said method comprising administering a nucleic acid that encodes hTERT to the subject by intradermal injection, and electrically transferring the nucleic acid into skin cells as follows:
   first, with a single pulse of High Voltage field strength of 1250 to 1400 V/cm and of duration of 10 µs to 1000 µs;
   second, with a single pulse of Low Voltage field strength of 100 to 200 V/cm and of duration of between 300 and 800 ms;
      wherein the nucleic acid encodes a TERT protein, and
      wherein the administration of the nucleic acid induces a cytotoxic T lymphocyte (CTL) response and the proliferation of cytotoxic CD8 T-cells and/or CD4 T-cells in the subject.

2. The method according to claim 1, wherein the single pulse of Low Voltage has a duration of between 350 and 600 ms.

3. The method according to claim 1, wherein the single pulse of High Voltage has a duration of between 50 and 150 µs.

4. The method according to claim 1, wherein the electrodes to be used are non-invasive plate electrodes.

5. The method according to claim 1, wherein the High Voltage pulse and the Low Voltage pulse are separated by a lag time.

6. The method according to claim 5, wherein the lag time is of between 300 ms and 3000 ms.

7. The method according to claim 1, wherein the nucleic acid is a single-stranded RNA or a double-stranded DNA.

8. The method according to claim 5, wherein the lag time is of between 500 ms and 1200 ms.

9. The method according to claim 5, wherein the lag time is of 1000 ms.

10. The method according to claim 1, wherein the single pulse of High Voltage is of 1250 V/cm.

11. The method according to claim 1, wherein the administration and electrical transfer of the nucleic acid induces a higher CTL response as compared to electrical transfer performed with a single pulse of High Voltage field strength of 1000 V/cm followed by a single pulse of Low Voltage field strength of 140 V/cm.

12. The method according to claim 1, wherein the nucleic acid encodes hTERT fused to a ubiquitin protein sequence.

13. The method according to claim 1, wherein the hTERT is enzymatically inactive.

14. The method according to claim 13, wherein the hTERT lacks VDD in the catalytic site.

15. The method according to claim 1, wherein the nucleic acid does not encode the nucleolar localization signal of hTERT.

* * * * *